United States Patent [19]

Nelson

[11] 4,424,368

[45] * Jan. 3, 1984

[54] PROCESS FOR MAKING PHOSPHORUS DERIVATIVES OF AMINOTHIOMETHYLCARBAMATES

[75] Inventor: Stephen J. Nelson, Comstock Township, Kalamazoo County, Mich.

[73] Assignee: The Upjohn Company, Kalamazoo, Mich.

[ * ] Notice: The portion of the term of this patent subsequent to Jul. 21, 1998, has been disclaimed.

[21] Appl. No.: 389,731

[22] Filed: Jun. 18, 1982

Related U.S. Application Data

[60] Division of Ser. No. 170,342, Jul. 21, 1980, Pat. No. 4,354,975, which is a continuation of Ser. No. 43,277, Jun. 1, 1979, abandoned.

[51] Int. Cl.$^3$ .................. C07D 307/82; C07D 339/00; C07F 9/24

[52] U.S. Cl. ........................................ 549/220; 549/5; 260/971

[58] Field of Search ..................... 549/5, 220; 260/971

[56] References Cited

U.S. PATENT DOCUMENTS 4,234,521  11/1980  Nelson ................................ 260/937
4,354,975  10/1982  Nelson ................................ 549/220

*Primary Examiner*—Anton H. Sutto
*Attorney, Agent, or Firm*—Joan Thierstein; Sidney B. Williams, Jr.

[57] ABSTRACT

This invention pertains to novel processes for preparing phosphorus derivatives of aminothiomethylcarbamates using as intermediates corresponding phosphorus derivatives of aminothiocarbamic halides. The carbamates are useful as pesticides against insects, mites, and nematodes. Two processes for preparing the corresponding intermediates are described. One preparation generally reacts an appropriate N-chlorothiophosphoramide with N-methylcarbamoyl halide. The other preparation generally reacts an N-chlorothiomethylcarbamoyl halide with an appropriate phosphoramide. The intermediate will react with various alcohols to produce the desired carbamates in the process of the invention.

51 Claims, No Drawings

PROCESS FOR MAKING PHOSPHORUS DERIVATIVES OF AMINOTHIOMETHYLCARBAMATES

This is a divisional of United States application Ser. No. 170,342, filed July 21, 1980, now U.S. Pat. No. 4,354,975, which is a continuation of United States application Ser. No. 043,277, filed June 1, 1979, now abandoned.

DESCRIPTION

Summary of the Invention

This invention pertains to novel processes for preparing phosphorus derivatives of aminothiomethylcarbamates. The invention is also particularly directed to the use of phosphorus derivatives of aminothiocarbamic halides as intermediates in these processes. Furthermore, the intermediates are compounds which insofar as is presently known, no one has previously prepared. Finally, processes of preparing the intermediates are novel. The invention also includes an improved process for making N-methylcarbamoyl fluoride which is a reactant therein.

BACKGROUND OF THE INVENTION

N-[(phosphinyl)amino]thio- and N-[(phosphinothioyl)amino]thiomethylcarbamates, a process for preparation and formulations of them suitable for pesticidal use are shown in U.S. Pat. No. 4,081,536 issued Mar. 28, 1978. Phosphoroaminosulfenyl derivatives of benzofuran carbamates and preparation thereof are disclosed in U.S. Pat. No. 4,024,277 issued May 17, 1977. These phosphorus acid derivatives of aminothiomethylcarbamate pesticides are among the compounds prepared by the novel processes of the present invention and, therefore, the above patents can be referred to for relevant status of the art.

Other prior art includes a detailed report describing the synthesis of dialkylaminothio derivatives of N-methylcarbamates by C. E. Hatch in J. Org. Chem., 43, 3953 (1978) which utilizes dialkylaminothiocarbamoyl fluorides in the synthesis of carbamate derivatives. This report also describes a preparation of N-methylcarbamoyl fluoride which contrary to the present invention uses solvents and excess hydrogen fluoride in the preparation thereof. Production of another carbamic acid fluoride is found in a process of Switzerland 422,755 claiming a German filing date of Feb. 20, 1961 by Farbenfabriken Bayer A. G. as disclosed in Derwent Abstract No. H1400 (=11,603). This process provides for the use of hydrogen fluoride as reactant and solvent, optionally with other solvent in a reaction with a substituted phenyl isocyanate thus also not teaching the advantages of the invention described herein.

Disclosures of a preparation for N-chlorothio-N-methylcarbamoyl fluoride and a preparation for N-chlorothio-N-methyl carbamoyl chloride, subsequently denoted as Formula IV herein are found in German Offenlegungsschriften Nos. 1,931,054 and 2,023,079 (fluoride) and U.S. Pat. No. 3,699,163 (chloride).

Further background teaching phosphoramide reactants denoted as Formula V herein is found in Methoden der Organischen Chemie (Houben-Weyl) Vol. 12, part 2, pages 610, 760 (thiophosphoramides) and pages 276, 413 (phosphoramides) Georg Thieme Verlag (Pub.), Stutgart, Germany, 1963. In addition L. Anschiitz et al., Ber. 61, 1264 (1928) teaches a benzothiophosphol chloride from which the corresponding amides of this invention can be made.

DETAILED DESCRIPTION OF THE INVENTION

The present invention is a process for preparing compounds having the formula:

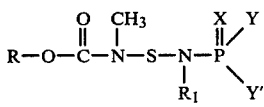

wherein R is selected from the group consisting of

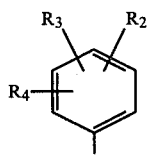

wherein $R_2$, $R_3$ and $R_4$ are the same or different and are selected from the group consisting of hydrogen, lower-alkyl of one to five carbon atoms, inclusive, halogen, lower-alkoxy of one to five carbon atoms, inclusive, lower-alkylthio of one to five carbon atoms, inclusive, dialkylamino with each alkyl the same or different and having one to three carbon atoms, inclusive, and $N=CHN(CH_3)_2$;

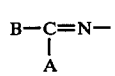

wherein A and B are the same or different and are selected from the group consisting of lower-alkyl of one to five carbon atoms, inclusive, lower-alkylthio of one to five carbon atoms, inclusive, phenylthio wherein phenyl is unsubstituted or substituted with one to three substituents, same or different, selected from the group consisting of halogen and lower-alkyl of one to four carbon atoms, inclusive, monocyano substituted alkylthio of one to five carbon atoms, inclusive, cyano, alkoxy having one to five carbon atoms, inclusive, phenyl, and hydrogen, with the proviso that when A is hydrogen, B is of the formula:

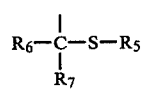

wherein $R_5$ is selected from the group consisting of alkyl of one to three carbon atoms, inclusive, and phenyl; $R_6$ is alkyl of one to three carbon atoms, inclusive; $R_7$ is selected from the group consisting of alkyl of one to three carbon atoms, inclusive, and $SR_8$, wherein $R_8$ is alkyl and is the same alkyl group as $R_5$, and taking $R_5$ and $R_8$ together with the atoms to which they are attached form a dithio heterocyclic of the formula:

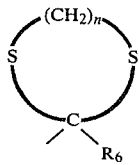

wherein n is 2 or 3 and the alkylene portion of the ring is unsubstituted or substituted with one or two methyl groups; A and B taken together with the carbon atom to which they are attached form a dithio heterocyclic of the formula:

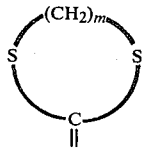

wherein m is 2 or 3 and the alkylene portion of the ring is unsubstituted or substituted with one to two methyl groups,; and

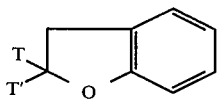

wherein T and T' can be the same or different and are selected from the group consisting of hydrogen and lower alkyl of from one to six carbons; $R_1$ is selected from the group consisting of lower-alkyl, phenyl, substituted phenyl, phenyl lower-alkyl, and cycloalkyl; X is oxygen or sulfur; Y and Y' are the same or different and are selected from the group consisting of $Y_1$ and $Y_1'$   $I_1$ and Y and y' taken together to form a functionality selected from the group consisting of:

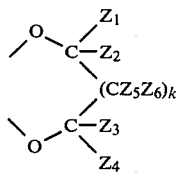 I'

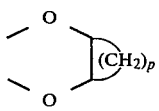

and

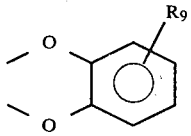 I''' wherein $Y_1$ and $Y_1'$ are selected from the group consisting of lower-alkyl, lower-alkoxy, lower-alkylthio, cycloalkyl, phenyl, substituted phenyl, phenoxy, substituted phenoxy, thiophenoxy, and substituted thiophenoxy; $Z_1$ through $Z_6$ are the same or different and are selected from the group consisting of hydrogen, methyl and ethyl; and k is 0 or 1, p is three or four and $R_9$ is selected from the group consisting of hydrogen, lower alkyl, lower alkoxy and halogen; which comprises:

(Step 1) preparing an intermediate having the formula:

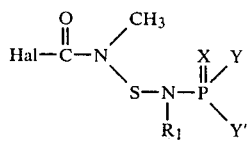 II wherein Hal is selected from the group consisting of fluoro and chloro; and $R_1$, X, Y and Y' are as defined for Formula I above;

(Step 2) reacting the intermediate with a compound having the formula:

ROH wherein R is as defined for Formula I above.

In the foregoing designation of variables, "lower-alkoxy" means methoxy, ethoxy, propoxy, isopropoxy, butoxy, pentoxy, and the further isomeric forms thrreof. Likewise, "lower-alkylthio" means methylthio, ethylthio, propylthio, isopropylthio, butylthio, pentylthio, and further isomeric forms thereof.

"Lower-alkyl" means methyl, ethyl, propyl, butyl, pentyl, and the isomeric forms thereof; while "cycloalkyl" means cyclopropyl, cyclobutyl, cyclopentyl, cyclohexyl optionally substituted with methyl, ethyl and propyl to a total of nine carbon atoms.

"Phenlower-alkyl" means benzyl, phenethyl, phenpropyl, phenbutyl, phenpentyl and isomeric forms thereof.

"Substituted-phenyl" means lower-alkyl, lower-alkoxy, halogen, nitro, and cyano-substituted-phenyl. There can be combinations of substituents such as 4-propyl-2-methyl, 2-chloro-4-methyl, 3,4-diethoxy, 3-cyano-4-ethoxyphenyl. Practically speaking, the "substituted-phenyl" group is limited to a total of ten carbon atoms, e.g., 4-isobutylphenyl.

"Substituted phenoxy" means lower-alkyl, lower-alkoxy, halogen, nitro and cyano substituted phenoxy. There can be combinations of substituents such as 4-propyl-2-methyl-, 2-chloro-4-methyl, 3,4-diethoxy, 3-cyano-4-ethoxy, and the like. The substituted phenoxy is limited to a total of ten carbon atoms, e.g. 4-isobutylphenoxy.

"Substituted thiophenoxy" means lower-alkyl, lower-alkoxy, halogen, nitro, and cyano substituted thiophenoxy. There can be combinations of substituents such as 4-propyl-2-methyl-, 2-chloro-4-methyl, 3,4-diethoxy. The substituted thiophenoxy is limited to a total of ten carbon atoms, e.g., 4-isobutylthiophenoxy.

The above (Step 2) reaction of hydroxy compounds with phosphorus derivatives of aminothiocarbamic halide intermediates having Formula II is conducted in an inert solvent, preferably an aprotic polar solvent such as acetonitrile, diethylether, tetrahydrofuran and dimethyl formamide and in the presence of an organic base, such as trialkyl amine (e.g., triethylamine), pyridine and lutidine, at temperatures from 0° to 100°, preferably 10° to 50°. Alternatively the reaction may be conducted in a two phase system consisting of an inert organic solvent such as toluene or methylene chloride and an aqueous phase in which the hydroxy compound, an alkali metal hydroxide and a phase transfer reagent are dissolved. Suitable phase transfer reagents include tetraalkylammonium halides, crown ethers and benzyltrimethylammonium chloride. The reaction is conducted at 0° to 100°, preferably 20° to 50°. The product of the invention process is isolated by conventional means such as by filtration, solvent evaporations, crystallization or chromatography.

Novel compounds of the invention are the intermediates II having the formula selected from the group consisting of:

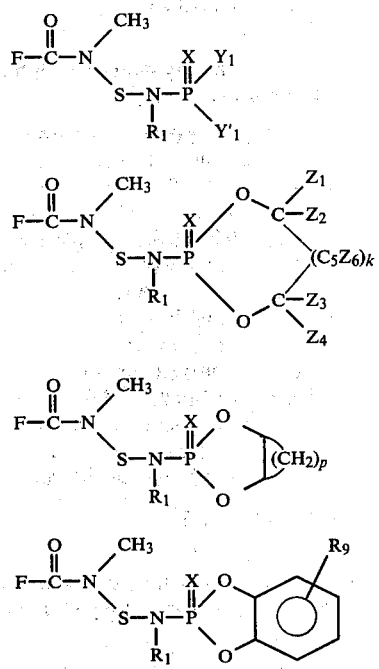

wherein $R_1$ and $R_9$, $Z_1$ through $Z_6$, X, $Y_1$, $Y_1'$, k, p and Hal are the same as defined above.

The new carbamic halide intermediates of this invention having the Formula II, are prepared in accordance with one of two processes. A schematic representation of one process is shown as follows:

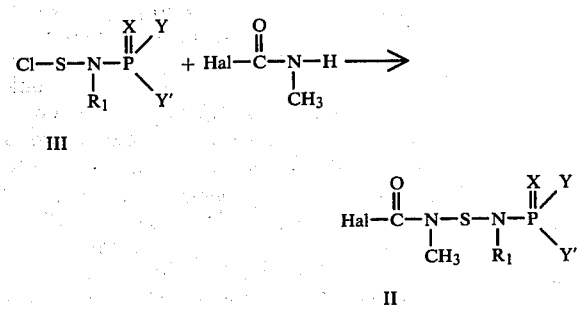

wherein $R_1$, X, Hal, Y and Y' are as defined for Formula I above. An alternative process may be represented schematically as follows:

SCHEME B

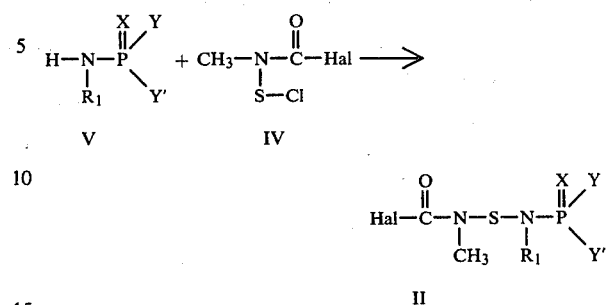

wherein $R_1$, X, Hal, Y and Y' are also as defined for Formula I above.

The N-methylcarbamyl halide reactant used in Scheme A includes both N-methylcarbamoyl fluoride and N-methylcarbamoyl chloride. These reactants are well known in the art as indicated above, however, the present invention also includes an improved method of making N-methylcarbamoyl fluoride.

It is known that N-methylcarbamoyl fluoride can be made in the following way:

$$HF + CH_3NCO \rightarrow CH_3NHCOF.$$

However, heretofore, solvents such as pentane or ether were employed in making it so that the product mixture could be stored and handled in conventional glassware.

It has now been discovered that N-methylcarbamoyl fluoride is readily obtained according to the above representation but in high yield and purity using conventional glassware by the addition of anhydrous hydrogen fluoride to a 0 to 50% excess and preferably 5 to 20% excess of methyl isocyanate in the absence of other solvent and at temperatures from −50° to +50° C., preferably at −20° to 20° C. In addition to the improvement in the method such that it can be carried out in the absence of a solvent, the procedure is now amenable to flow type reactors in gas or condensed phase, thereby confining the reaction to a relatively small volume which also provides the advantages of efficient cooling and confinement of hazardous materials to a small space.

N-chlorothiophosphoramide type compounds of Formula III for use in Scheme A are known in the art as disclosed in U.S. Pat. Nos. 4,024,277 and 4,081,536 or can be readily obtained by using appropriate starting materials in the procedures described therein. These appropriate starting materials are described as phosphoramide V reactants above.

Reaction of compounds of Formula III with N-methylcarbamoyl halide is performed in an inert solvent, preferably a polar aprotic solvent such as acetonitrile or dimethyl formamide, and in the presence of a tertiary organic base such as triethylamine as an acid acceptor. The temperature of the reaction may be −50° to +40°, preferably −30° to +10°. The resultant phosphorus amide type thiocarbamic halide intermediates having Formula $II_1$, II', II'', and II''' are isolated by conventional means and are suitable as the intermediates as obtained in a crude state for reaction with hydroxy compounds in Step 2 above.

The alternative procedure, Scheme B, to obtain the desired intermediate II reacts an N-chlorothiomethylcarbamoyl halide IV with an appropriate phosphoramide V. The reaction is conducted in a suitably inert solvent such as dimethyl formamide, acetonitrile, ether, tetrahydrofuran, toluene, or methylene chloride in the presence of an organic base such as triethylamine, at temperatures from −20° to 50° C., preferably at −20° to 10° C. The intermediates prepared by this means are also isolated by conventional means and are suitable as obtained, i.e. without purification, for reaction with hydroxy compounds in Step 2 above.

Although it is indicated above that the novel intermediates are isolated in each scheme, it is not necessary to separate the intermediates from the reaction mixture of their preparation before further reaction with hydroxy compounds according to the process of this invention in obtaining the desired product, Formula I supra.

The following Examples of an improved method of preparation for N-methylcarbamoyl fluoride, novel phosphorus derivatives of aminothiocarbamic halide intermediate having the Formula selected from the group consisting of $II_1$, $II'$, $II''$, $II'''$, preparations thereof and processes therefore that are novel for the preparation of a desired product having formula I are indicative of the scope of this invention and are not to be construed as limitative. Those skilled in the art wil promptly recognize appropriate variations from the procedure both as to methylcarbamate precursors as well as reaction conditions and techniques. These examples indicate the best mode presently known to the inventor.

EXAMPLE A  N-methylcarbamoyl fluoride

An Improved Method of Preparation

Anhydrous hydrogen fluoride (21.8 g, 1.09 mol) is passed through polyethylene tubing into methyl isocyanate (72.5 g, 1.27 mol) cooled in an ice-methanol bath at −10° using ordinary glass equipment. After the addition is complete the excess methyl isocyanate is removed at 25° and 40–60 mm to leave the product as a clear colorless liquid (83.75 g, 99.7%). The material distills at 48°, 10 mm.

EXAMPLE 1

Methyl N-[[[[[(diethoxyphosphinothioyl)-1-isopropylamino]thio]methylamino]carbonyl]oxy]ethanimidothioate. $I_1$ A solution of triethylamine (2.00 ml, 14.3 mmol) in dimethylformamide (5 ml) is added over 5 minutes to a solution of diethoxy N-chlorothio(isopropyl)thiophosphoramide (4.07 g, 14.7 mmol) and N-methylcarbamoyl fluoride (1.11 g, 15.0 mmol) in dimethylformamide (15 ml) cooled in an ice bath. After the addition the mixture is stirred at 0° for two hours then diluted with ice cold saturated sodium bicarbonate and extracted with hexanes. The extract is dried over magnesium sulfate and concentrated under reduced pressure to leave a yellow oil. The material is chromatographed through a Merck size C Lobar column eluting with 2.5% ethyl acetate in hexanes to give the intermediate $II_1$, O,O-diethyl isopropyl[[(fluorocarbonyl)methylamino]thiophosphoramidothioate, as a yellow oil. The ir spectrum shows a $\gamma C{=}O$ at 1790 cm−1 and the pmr spectrum displays a doublet (J=1 cps) for the N—CH$_3$. A two-way tlc of the purified product indicates the material to be unstable toward chromatography on silica gel. The purified O,O-diethyl isopropyl[[(fluorocarbonyl)methylamino]thio]phosphoramidothioate (0.56 g, 1.8 mmol), methyl N-hydroxyethanimidothioate (0.22 g, 2.1 mmol), and triethylamine (0.3 ml, 2.2 mmol) are dissolved in acetonitrile (1.5 ml) and the solution kept at room temperature for 17 hours, diluted with a one to one mixture of ethyl acetate-Skellysolve B, washed with water, dried over magnesium sulfate and concentrated under reduced pressure. The residual yellow oil is crystallized from ether-Skellysolve B to give a yellow solid (0.43 g), m.p. 65°–7°. A second recrystallization gives material of m.p. 69°–71°, undepressed on admixture with a corresponding sample prepared according to the procedures disclosed in U.S. Pat. No. 4,081,536. The pmr and ir spectra are identical to material prepared from methyl N-[[(methylamino)carbonyl]oxy]ethanimidothioate. (See the fifth compound in Example 5, U.S. Pat. No. 4,081,536).

PREPARATION 1

O,O-diethyl isopropyl[[[(fluorocarbonyl)methylamino]thio]phosphoramidothioate $II_1$ A solution of O,O-diethyl isopropylphosphoramidothioate (14.9 g, 70.8 mmol) and triethylamine (9.8 ml, 70.8 mmol) in tetrahydrofuran (50 ml) is added dropwise over 10 minutes to a solution of N-chlorothio(methyl)carbamoyl fluoride (10.2 g, 70.8 mmol) in tetrahydrofuran (50 ml) cooled in an ice bath. After the addition the mixture is stirred for 1.5 hours at 0°, diluted with ether (200 ml), washed with ice cold water, dried over sodium sulfate and concentrated under reduced pressure. The residue shows identical absorptions in the ir and pmr spectra for $\gamma$ C=O and N—CH$_3$ as obtained for the yellow oil that is intermediate $II_1$ of Example 1. The crude $II_1$ product is suitable for reaction with methyl N-hydroxyethanimidothioate as in Example 1.

EXAMPLE 2

Methyl N-[[[methyl[[isopropyl(2-thioxo-1,3,2-dioxaphosphorinan-2-yl)amino]thio]amino]carbonyl]oxy]ethanimidothioate. $I'$ A solution of 2-(isopropylamino)-2-thioxo-1,3,2-dioxaphosphorinane (13.0 g, 66.6 mmol) and triethylamine (7.3 g, 72 mmol) in tetrahydrofuran (50 ml) is added dropwise over 10 minutes to a solution of sulfur dichloride (8.1 g, 78.7 mmol) in tetrahydrofuran (50 ml) with cooling to maintain a temperature of −5 to 0°. After the addition the mixture is stirred for two hours then diluted with ether (100 ml). The reaction mixture is filtered under nitrogen and the filtrate concentrated under reduced pressure. The residual oil is dissolved in dimethyl formamide (50 ml) and N-methylcarbamoyl fluoride (5.8 g, 75.3 mmol) added at once followed by dropwise addition of triethylamine (7.3 g, 72 mmol) in dimethyl formamide (10 ml) over 10 minutes with cooling in a bath at −25°. After the addition the mixture is stirred for two hours in a bath at 0°. The mixture is diluted with ether, washed with ice cold water, dried and concentrated to leave the crude N-methyl[[(isopropyl)2-thioxo-1,3,2-dioxaphosphorinan-2-yl)amino]thio]carbamic fluoride $II'$ as a red oil. The pmr spectrum (CDCl$_3$) of this material exhibits a doublet (J$_{F-H}$=1 cps) for N—CH$_3$ centered at 3.45 ppm. The infrared spectrum shows $\gamma$ C=O at 1785 cm−1. The carbamic fluoride $II'$ is dissolved in methylene chloride (50 ml.) and a solution of methyl N-hydroxyethanimidothioate (7.00 g, 66.6 mmol), tetraethylammonium chloride (1.00 g, 6.04 mmol) and sodium hydroxide (3.20 g, 80 mmol) in water (50 ml) is added at once. The mixture is stirred for 20 hours at room temperature, the phases separated, and the organic phase washed with water, dried over magnesium sulfate and concentrated under reduced pressure. The residual oil is triturated with ether to preecipitate methyl N-[[[methyl-[[isopropyl(2-thioxo-1,3,2-dioxaphsophorinan-2-yl)amino]thio]amino]carbonyl]oxy]ethanimidothioate I' (3.90 g, 15%) as a white solid. The pmr and ir spectra are identical to corresponding material prepared from methyl N-[[(methylamino)carbonyl]oxy]ethanimidothioate according to the procedures disclosed in U.S. Pat. No. 4,081,536. m.p. 153°–154° C.

PREPARATION 2

Preparation of N-methyl[[(isopropyl)(2-thioxo-1,3,2-dioxaphosphorinan-2-yl)amino]thio]carbamic fluoride II' using N-chlorothio(methyl)carbamic fluoride.

A solution of 2-(isopropylamino)-2-thioxo-1,3,2-dioxaphosphorinane (13.8 g, 70.8 mmol) and triethylamine (9.8 ml), 70.8 mmol) in tetrahydrofuran (50 ml) is added dropwise over 10 minutes to a solution of N-chlorothio(methyl)carbamoyl fluoride (10.2 g, 70.8 mmol) in tetrahydrofuran (50 ml) cooled in an ice bath. After the addition the mixture is stirred for 1.5 hours at 0°, diluted with ether (200 ml), washed with ice cold water, dried over sodium sulfate and concentrated under reduced pressure. The residue shows identical absorptions in the ir and pmr spectra for $\gamma$ C=O and N—CH$_3$ as obtained from the carbamic fluoride intermediate II' of Example 2. This crude N-methyl[[(isopropyl)(2-thioxo-1,3,2-dioxaphosphorinan-2-yl)amino]thio]carbamic fluoride II' using N-chlorothio(methyl)carbamic fluoride is also suitable for reaction with methyl N-hydroxyethanimidothioate as in Example 2.

EXAMPLE 3

Methyl N-[[[[[(5,5-dimethyl-1,3,2-dioxaphosphorinan-2-yl)(tert-butyl)amino]thio]methylamino]carbonyl]oxy]ethanimidothioate. II'

Following the procedure given in Example 2 but using 2-N-[chlorothio(tert-butyl)amino]-5,5-dimethyl-2-thioxo-1,3,2-dioxaphosphorinane which is prepared from 2-(tert-butylamino)-2-thioxo-1,3,2-dioxaphosphorinane and sulfur dichloride the title compound II' is obtained. The pmr and ir spectra are identical to corresponding material prepared from methyl N-[[(methylamino)carbonyl]oxy]ethanimidoate according to the procedure in U.S. Pat. No. 4,081,536. m.p. 167°–168.5° C.

Analysis: Calc'd for: C$_{14}$H$_{28}$N$_3$O$_4$PS$_3$: C, 39.14; H, 6.57; N, 9.78. Found: C, 39.45; H, 6.73; N, 9.87.

PREPARATION 3

N-methyl[[(tert-butyl)(2-thioxo-1,3,2-dioxaphosphorinan-2-yl)amino]thio]carbamic fluoride, II', using N-chlorothio(methyl)carbamic fluoride Following the procedure given in Preparation 2 but using 2-(tert-butylamino)-2-thioxo-1,3,2-dioxaphosphorinane, the intermediate, II', is obtained which may be substituted in the procedures of Example 3 for reaction with methyl N-hydroxyethanimidothioate to obtain methyl N-[[[[[(5,5-dimethyl-1,3,2-dioxaphosphorinan-2-yl)(tert-butyl)amino]thio]methylamino]carbonyl]oxy]ethanimidothioate. I'

EXAMPLE 4

2-(isopropyl)phenyl [[cyclopentyl(3a,4,5,6,7,7a-hexahydro-2-oxo-1,3,2-benzodioxaphosphol-2-yl)amino]thio]methylcarbamate I''

A solution of N-cyclopentyl-3a,4,5,6,7,7a-hexahydro-2-oxo-1,3,2-benzodioxaphosphol-2-amine (16.3 g, 66.6 mmol) and triethylamine (7.3 g, 72 mmol) in tetrahydrofuran (50 ml) is added dropwise over 10 minutes to a solution of sulfur dichloride (8.1 g, 78.7 mmol) in tetrahydrofuran (50 ml) with cooling to maintain a temperature of −5° to 0°. After the addition the mixture is stirred for two hours then diluted with ether (100 ml). The reaction mixture is filtered under nitrogen and the filtrate concentrated in vacuo. The residue is dissolved in dimethyl formamide (50 ml) and N-methyl carbamoyl fluoride (5.8 g, 75.3 mml) added at once followed by dropwise addition of triethylamine (7.3 g, 72 mmol) in dimethyl formamide (10 ml) over 10 minutes with cooling in a bath at −25°. After the addition the mixture is stirred for two hours in a bath at 0°. The mixture is diluted with ether, washed with ice cold water, dried and concentrated to leave crude N-methyl[[(cyclopentyl)(3a,4,5,6,7,7a-hexahydro-2-oxo-1,3,2-benzodioxaphosphol)amino]thio]carbamic fluoride II''. The carbamoyl fluoride II'' is dissolved in methylene chloride (50 ml) and a solution of methyl N-hydroxyethanimidothioate (7.00 g, 66.6 mmol), tetraethylammonium chloride (1.00 g, 6.04 mmol) and sodium hydroxide (3.20 g, 80 mmol) in water (50 ml) is added at once. The mixture is stirred for 20 hours at room temperature, the phases separated, and the organic phase washed with water, dried over magnesium sulfate and concentrated under reduced pressure. The residual oil is triturated with ether to precipitate the product 2-(isopropyl)phenyl[[(cyclopentyl(3a,4,5,6,7a-hexahydro-2-oxo-1,3,2-benzodioxaphosphol-2-yl)amino]thio]methylcarbamate I''.

PREPARATION 4

N-methyl[[(cyclopentyl)(3a,4,5,6,7,7a-hexahydro-2-oxo-1,3,2-benzodioxaphosphol)amino]thio]carbamic fluoride II''

A solution of N-cyclopentyl-3a,4,5,6,7,7a-hexahydro-2-oxo-1,3,2-benzodioxaphosphol-2-amine (17.36 g, 70.8 mmol) and triethylamine (9.8 ml, 70.8 mmol) in tetrahydrofuran (50 ml) is added dropwise over 10 minutes to a solution of N-chlorothio(methyl)carbamoyl fluoride (10.2 g, 70.8 mmol) in tetrahydrofuran (50 ml) cooled in an ice bath. After the addition the mixture is stirred for 1.5 hours at 0°, diluted with ether (200 ml), washed with ice cold water, dried over sodium sulfate and concentrated under reduced pressure. The identical absorptions in the ir and pmr spectra for $\gamma$ C=O and N—CH$_3$ as obtained for the carbamoyl fluoride intermediate II'' of Example 4. This crude N-methyl[[(cyclopentyl)-(3a,4,5,6,7,7a-hexahydro-2-oxo-1,3,2-benzodioxaphosphol)amino]thio]carbamic fluoride I'' is suitable for reaction with methyl N-hydroxyethanimidothioate as in Example 4 above.

EXAMPLE 5

Methyl N-[[[methyl[[(2-methylpropyl)(2-thioxo-1,3,2-benzodioxaphosphol-2-yl)amino]thio]amio]carbonyl]oxy]ethanimidothioate. I'''

A solution of N-(2-methylpropyl)-2-thioxo-1,3,2-benzodioxaphosphol-2-amine (16.2 g, 66.6 mmol) and triethylamine (7.3 g, 72 mmol) in tetrahydrofuran (50 ml) is added dropwise over 10 minutes to a solution of sulfur dichloride (8.1 g, 78.7 mmol) in tetrahydrofuran (50 ml) with cooling to maintain a temperature of −5° to 0°. After the addition, the mixture is stirred for two hours then diluted with ether (100 ml). The reaction mixture is filtered under nitrogen and the filtrate concentrated in vacuo. The residue is dissolved in dimethyl formamide (50 ml) and N-methyl carbamoyl fluoride (5.8 g, 75.3 mmol) added at once followed by dropwise addition of triethylamine (7.3 g, 72 mmol) in dimethyl formamide (10 ml) over 10 minutes with cooling in a bath at −25° C. After the addition the mixture is stirred for two hours in a bath at 0°. The mixture is diluted with ether, washed with ice cold water, dried and concentrated to leave a crude N-methyl[[(2-methylpropyl)(2-thioxo-1,3,2-benzodioxaphosphol-2-yl)amino]thio]carbamic fluoride II'''. The carbamic fluoride is dissolved in methylene chloride (50 ml) and a solution of methyl N-hydroxyethanimidothioate (7.00 g, 66.5 mmol), tetraethylammonium chloride (1.00 g, 6.04 mmol) and sodium hydroxide (2.20 g, 80 mmol) in water (50 ml) is added at once. The mixture is stirred for 20 hours at room temperature, the phases separated, and the organic phase washed with water, dried over magnesium sulfate and concentrated under reduced pressure. The residual oil is triturated with ether to precipitate the product methyl N-[[[methyl[[(2-methylpropyl)(2-thioxo-1,3,2-benzodioxaphosphol-2-yl)amino]thio]amino]carbonyl]oxy]ethanimidothioate I'''.

PREPARATION

N-methyl[[(2-methylpropyl)(2-thioxo-1,3,2-benzodioxaphosphol-2-yl)amino]thio]carbamic fluoride II'''.

A solution of N-(2-methylpropyl)-2-thioxo-1,3,2-benzodioxaphosphol-2-amine (17.2 g, 70.8 mmol) and triethylamine (9.8 ml, 70.8 mmol) in tetrahydrofuran (50 ml) is added dropwise over 10 minutes to a solution of N-chlorothio(methyl)carbamoyl fluoride (10.2 g, 70.8 mmol) in tetrahydrofuran (50 ml) cooled in an ice bath. After the addition the mixture is stirred for 1.5 hours at 0°, diluted with ether (200 ml), washed with ice cold water, dried over sodium sulfate and concentrated under reduced pressure. The residue shows identical absorptions in the ir and pmr spectra for γ C=O and N—CH$_3$ as obtained for the carbamic fluoride II''' of Example 5. This crude carbamoyl fluoride product is suitable for reaction with methyl N-hydroxyethanimidothioate as in Example 5.

Following the procedures in Example 2 or Preparation 2 the intermediate N-methyl[[(isopropyl)(2-thioxo-1,3,2-dioxaphosphorinan-2-yl)amino]thio]carbamic fluoride II' is prepared and further reacted according to the procedures in Example 2 but using 2,3-dihydro-2,2-dimethyl-7-benzofuranol to obtain 2,3-dihydro-2,2-dimethyl-7-benzofuranyl[[isopropyl(2-thioxo-1,3,2-dioxaphosphorinan-2-yl)amino]thio]methylcarbamate.

Infrared and pmr spectra consistent with expected product:

Calc'd for $C_{18}H_{23}N_2O_4PS_2$ 426.494. C, 50.69, H, 5.44, N, 6.57. Found: C, 50.73, H, 5.97, N, 6.52.

Mass spectrum shows molecular ion 426.

Examples 1 through 5 use a process for preparing compounds having Formula I through a novel intermediate II prepared by the reaction as shown in Scheme A. Preparations 1 through 5 prepare the same novel intermediates II by the reaction as shown in Scheme B, which can then be used in Examples 1 through 5 for the preparation of Formula I compounds. Thus, preparation of Formula I compounds can be accomplished by a process including the preparation of novel intermediates using Scheme A or using Scheme B. Therefore it is understood that novel processes to make compounds I of this invention are made through Scheme A or Scheme B described herein.

Appropriate starting materials are substituted in Example 1 and Preparation 1 according to the processes as described herein to prepare corresponding novel intermediates II$_1$ of the invention as follows:

O,O-di-n-propyl methyl[[(fluorocarbonyl)methylamino]thio]phosphoramidothioate,

O,O-di-n-propyl n-propyl[[(fluorocarbonyl)methylamino]thio]phosphoramidothioate, O,O-dimethyl ethyl[[(fluorocarbonyl)methylamino]thio]phosphoramidothioate, O,O-diisopropyl methyl[[(fluorocarbonyl)methylamino]thio]phosphoramidothioate, O,O-diphenyl methyl[[(fluorocarbonyl)methylamino]thio]phosphoramidothioate, O,O-diethyl ethyl [[(fluorocarbonyl)methylamino]thio]phosphoramidothioate, O,O-diethyl 2-phenylethyl[[(fluorocarbonyl)methylamino]thio]phosphoramidothioate, O,O-diethyl propyl[[(fluorocarbonyl)methylamino]thio]phosphoramidothioate, O,O-diethyl isopropyl[[(fluorocarbonyl)methylamino]thio]phosphoramidothioate, O,O-dimethyl methyl[[(fluorocarbonyl)methylamino]thio]phosphoramidothioate, O,O-dimethyl isopropyl [[(fluorocarbonyl)methylamino]thio]phosphoramidothioate, O,O-diethyl methyl[[(fluorocarbonyl)methylamino]thio]phosphoramidothioate, O,O-diethyl isopropyl[[(fluorocarbonyl)methylamino]thio]phosphoramidothioate, O,O-diethyl n-propyl[[(fluorocarbonyl)methylamino]thio]phosphoramidothioate, O,O-diethyl methyl[[(fluorocarbonyl)methylamino]thio]phosphoramidoate, O,O-diethyl phenyl[[(fluorocarbonyl)methylamino]thio]phosphoramidothioate, O,S-dimethyl methyl[[(fluorocarbonyl)methylamino]thio]phosphoramidothiate, O-methyl-N-isorpopyl-N-[[(fluorocarbonyl)methylamino]thio]-P-phenylphosphonamidothioate, O-methyl-N-methyl-N-[[(fluorocarbonyl)methylamino]thio]-P-phenylphosphonamidothioate, O-methyl-N-methyl-N-[[(fluorocarbonyl)methylamino]thio]-P-methylphosphonamidothioate, O-isopropyl-N-isopropyl-N-[[(fluorocarbonyl)methylamino]thio]-P-phenylphosphonamidothioate, O-phenyl-N-methyl-N-[[(fluorocarbonyl)methylamino]thio]-P-methylphosphonamidothioate, O-isopropyl-N-isopropyl-N-[[(fluorocarbonyl)methylamino]thio]-P-methylphosphonamidothioate, O-methyl-N-isopropyl-N-[[(fluorocarbonyl)methylamino]thio]-P-methylphosphonamidothioate, O-phenyl-N-isopropyl-N-[[(fluorocarbonyl)methylamino]thio]-P-methylphosphonamidothioate,
O-phenyl-N-phenyl-N-[[(fluorocarbonyl)methylamino]thio]-P-ethylphosphonamidothioate,
O-4-chlorophenyl-N-isopropyl-N-[[(fluorocarbonyl)methylamino]thio]-P-methylphosphonamidothioate,
O-isopropyl-N-phenyl-N-[[(fluorocarbonyl)methylamino]thio]-P-methylphosphonamidothioate,
O-([1,1'-biphenyl]-4-yl)-N-isopropyl-N-[[(fluorocarbonyl)methylamino]thio]-P-ethylphosphonamidothioate,
O-phenyl-N-ethyl-N-[[(fluorocarbonyl)methylamino]thio]-P-phenylphosphonamidothioate,
O-phenyl-N-benzyl-N-[[(fluorocarbonyl)methylamino]thio]-P-ethylphosphonamidothioate,
O-phenyl-N-phenyl-N-[[(fluorocarbonyl)methylamino]thio]-P-ethylphosphonamidothioate,
O-ethyl-N-phenyl-N-[[(fluorocarbonyl)methylamino]thio]-P-phenylphosphonamidothioate,
O-phenyl-N-butyl-N-[[(fluorocarbonyl)methylamino]thio]-P-ethylphosphonamidothioate,
O-2-chlorophenyl-N-phenyl-N-[[(fluorocarbonyl)methylamino]thio]-P-ethylphosphonamidothioate,
O-4-chlorophenyl-N-phenyl-N-[[(fluorocarbonyl)methylamino]thio]-P-ethylphosphonamidothioate,
O-phenyl-N-cyclohexyl-N-[[(fluorocarbonyl)methylamino]thio]-P-ethylphosphonamidothioate.

In addition, appropriate starting materials are used in the above processes to prepare novel compounds II$_1$, as follows:
O-ethyl-O-phenyl[[(fluorocarbonyl)methylamino]thio]phosphoramidothioate,
O-ethyl-S-phenyl[[(fluorocarbonyl)methylamino]thio]phosphoramidothioate,
O,O-diethyl phenyl[[(fluorocarbonyl)methylamino]thio]phosphoramide,
O-phenyl-N-[[(fluorocarbonyl)methylamino]thio]-N-methyl-P-phenylphosphoramidothiate,
O-phenyl-N-[[(fluorocarbonyl)methylamino]thio]-N-p-nitrophenyl-P-methylphosphoramidothioate,
O-phenyl-N-[[(fluorocarbonyl)methylamino]thio]-N-o-methylphenyl-P-ethylphosphoramidothioate,
O-phenyl-N-[[(fluorocarbonyl)methylamino]thio]-N-m-trifluoromethylphenyl-P-ethylphosphoramidothioate,
O-phenyl-N-[[(fluorocarbonyl)methylamino]thio]-N-o-chlorophenyl-P-ethylphosphoramidothioate,
O-cyclohexyloxy-N-[[(fluorocarbonyl)methylamino]thio]-N-cyclohexyl-P-ethylphosphoramidothioate,
O-p-nitrophenyl-N-[[(fluorocarbonyl)methylamino]thio]-N-phenyl-P-ethylphosphoramidothioate,
O-ethyl-N-[[(fluorocarbonyl)methylamino]thio]-N-methyl-P-ethylphosphoramidothioate,
S-phenyl-N-[[(fluorocarbonyl)methylamino]thio]-N-methyl-P-ethylphosphoramidothioate,
N-[[(fluorocarbonyl)methylamino]thio]-N-methyl-P-p-chlorophenyl-P-methylphosphinamidothioate,
N-[[(fluorocarbonyl)methylamino]thio]-N-methyl-P,P-diethylphosphinamidothioate,
O-phenyl-N-[[(fluorocarbonyl)methylamino]thio]-N-methyl-P-phenylphosphonamide,
O-phenyl-N-[[(fluorocarbonyl)methylamino]thio]-N-methyl-P-ethylphosphonamidothioate,
O-phenyl-N-[[(fluorocarbonyl)methylamino]thio]-N-methyl-P-ethylphosphonamide,
O-ethyl-N-[[(fluorocarbonyl)methylamino]thio]-N-phenyl-P-ethylphosphonamide,
S-phenyl-N-[[(fluorocarbonyl)methylamino]thio]-N-phenyl-P-methylphosphonamidothioate.

Further, appropriate starting materials are substituted in Examples 2 and 3 and Preparations 2 and 3 according to the processes as described herein to prepare corresponding novel intermediates II' of the invention as follows:
[[isopropyl(5,5-dimethyl-2-thioxo-1,3,2-dioxaphosphorinan-2-yl)amino]thio]methylcarbamic fluoride,
[[isopropyl(5,5-diethyl-2-thioxo-1,3,2-dioxaphosphorinan-2-yl)amino]thio]methylcarbamic fluoride,
[[ethyl(5,5-dimethyl-2-thioxa-1,3,2-dioxaphosphorinan-2-yl)amino]thio]methylcarbamic fluoride,
[[isopropyl(2-thioxo-1,3,2-phospholan-2-yl)amino]thio]methylcarbamic fluoride,
[[isopropyl(4,4,6-trimethyl-2-thioxo-1,3,2-dioxaphosphorinan-2-yl)amino]thio]methylcarbamic fluoride,
[[cyclohexyl(5,5-diethyl-2-thioxo-1,3,2-dioxaphosphorinan-2-yl)amino]thio]methylcarbamic fluoride,
[[cyclohexyl(5,5-dimethyl-2-thioxo-1,3,2-dioxaphosphorinan-2-yl)amino]thio]methylcarbamic fluoride,
[[methyl(2-thioxo-1,3,2-dioxaphosphorinan-2-yl)amino]thio]methylcarbamic fluoride.

Other novel II' compounds are prepared by the processes herein as follows:
[[isopropyl(2-thioxo-4H-1,3,2-benzodioxaphosphorinan-2-yl)amino]thio]methylamino]methylcarbamic fluoride,
[[methyl(2-thioxo-1,3,2-dioxaphospholan-2-yl)amino]thio]methylcarbamic fluoride,
[[ethyl(hexahydro-2-oxo-1,3,2-benzodioxaphospholan-2-yl)amino]thio]methylcarbamic fluoride,
[[isopropyl(2-oxo-1,3,2-benzodioxaphopholan-2-yl)amino]thio]methylcarbamic fluoride,
[[benzyl(5,5-diethyl-2-thioxo-1,3,2-dioxaphosphorinan-2-yl)amino]thio]methylcarbamic fluoride,
[[methyl(2-thioxo-1,3,2-dioxaphosphorinan-2-yl)amino]thio]methylcarbamic fluoride.

Additionally, appropriate starting materials are substituted in Examples 4 and 5 and Preparations 4 and 5 according to the processes as described herein to prepare corresponding novel intermediates II'' and II''' within the scope of the invention.

Further, intermediates II', and II'' wherein X is oxygen, as well as, additional intermediates II$_1$ and II''' wherein X is also oxygen, are prepared by using appropriate starting materials in the processes according to each of the Examples and Preparations 1, 2, 3 and 4 respectively as described above. Intermediates II''' wherein X is sulfur may likewise be prepared by using corresponding starting materials in Example 5 and Preparation 5.

Finally, in the formulation of Compounds I prepared by the processes in the present invention for pesticidal utility conventional techniques are used as fully disclosed in U.S. Pat. Nos. 4,081,536 and in 4,024,277.

I claim:
1. A process for preparing a compound having the formula:

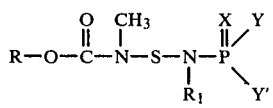

wherein R is selected from the group consisting of:

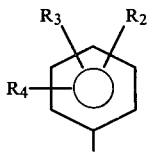
a.

wherein R, R, and R are the same or different and are selected from the group consisting of hydrogen, lower-alkyl of one to five carbon atoms, inclusive, halogen, lower-alkoxy of one to five carbon atoms, inclusive, lower-alkylthio of one to five carbon atoms, inclusive, dialkylamino with each alkyl the same or different and having one to three carbon atoms, inclusive, and $N=CHN(CH_3)_2$;

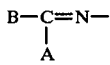
b.

wherein A and B are the same or different and are selected from the group consisting of lower-alkyl of one to five carbon atoms, inclusive, lower-alkylthio of one to five carbon atoms, inclusive, phenylthio wherein phenyl is unsubstituted or substituted with one to three substituents, same or different, selected from the group consisting of halogen and lower-alkyl of one to four carbon atoms, inclusive, monocyano substituted alkylthio of one to five carbon atoms, inclusive, cyano, alkoxy having one to five carbon atoms, inclusive, phenyl, and hydrogen, with the proviso that when A is hydrogen, B is of the formula:

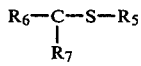

wherein $R_5$ is selected from the group consisting of alkyl of one to three carbon atoms, inclusive, and phenyl; $R_6$ is alkyl of one to three carbon atoms, inclusive; $R_7$ is selected from the group consisting of alkyl of one to three carbon atoms, inclusive, and $SR_8$, wherein $R_8$ is alkyl and is the same alkyl group as $R_5$, and taking $R_5$ and $R_8$ together with the atoms to which they are attached form a dithio heterocyclic of the formula:

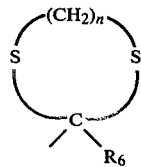

wherein n is 2 or 3 and the alkylene portion of the ring is unsubstituted or substituted with one or two methyl groups; A and B taken together with the carbon atoms to which they are attached form a dithio heterocyclic of the formula:

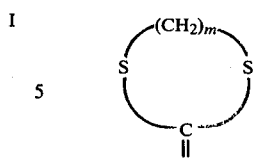

wherein m is 2 or 3 and the alkylene portion of the ring is unsubstituted or substituted with one to two methyl groups; and

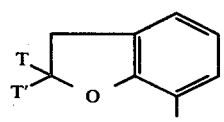
c.

wherein T and T' can be the same or different and are selected from the group consisting of hydrogen and lower alkyl of from one to six carbons; $R_1$ is selected from the group consisting of lower-alkyl, phenyl, substituted phenyl, phenyl lower-alkyl, and cyclo-alkyl; X is oxygen or sulfur; Y and Y' are the same or different and are selected from the group consisting of:

$Y_1$ and $Y'_1$      $I_1$ and

Y and Y' taken together to form a functionality selected from the group consisting of:

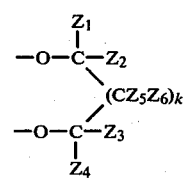
I'

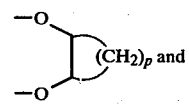
I''

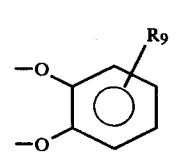
I''' wherein $Y_1$ and $Y'_1$ are selected from the group consisting of lower-alkyl, lower-alkoxy, lower-alkylthio, cycloalkyl, phenyl, substituted phenyl, phenoxy, substituted phenoxy, thiophenoxy, and substituted thiophenoxy, $Z_1$ through $Z_6$ are the same or different and are selected from the group consisting of hydrogen, methyl and ethyl; and k is 0 or 1, p is three or four and $R_9$ is selected from the group consisting of hydrogen, lower alkyl, lower alkoxy and halogen; which comprises (1) preparing an intermediate selected from the group consisting of:

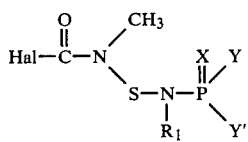

in a process wherein a compound having the formula

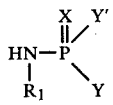     V is reacted with a compound having the formula

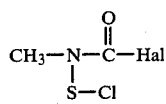     IV wherein $R_1$, X, Y and Y' are as defined for formula I and Hal is fluorine or chlorine and, (2) contacting the intermediate II with a compound having the formula ROH wherein R is the same as above.

2. A process according to claim 1 wherein Hal is fluorine.

3. A process according to claim 1 for preparing compounds having the formula:

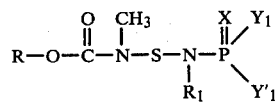     $I_1$ wherein R, $R_1$, X, $Y_1$ and $Y_1'$ are the same as in claim 2.

4. A process according to claim 3 wherein X is sulfur.

5. A process according to claim 3 wherein X is oxygen.

6. A process according to claim 4 wherein R is an alkanimido group of the kind:

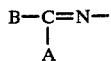

wherein A consists of lower alkyl and B consists of lower alkylthio.

7. A process according to claim 5 wherein both $Y_1$ and $Y_1'$ are lower-alkoxy.

8. A process according to claim 5 wherein $Y_1$ is lower-alkylthio and $Y_1'$ is lower-alkoxy.

9. A process according to claim 4 wherein R is:

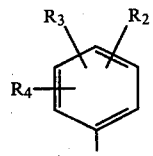

wherein $R_2$, $R_3$, and $R_4$ are the same or different and are selected from the group consisting of hydrogen, lower-alkyl, of one to five carbon atoms, inclusive, halogen, lower-alkoxy of one to five carbon atoms, inclusive, lower alkylthio of one to five carbon atoms, inclusive, dialkylamino with each alkyl the same or different and having one to three carbon atoms, inclusive, and $N=CHN(CH_3)_2$.

10. A process according to claim 9 wherein the compound I prepared is selected from the group consisting of:

4-(dimethylamino)-3,5-xylyl [[diethoxyphosphinothioyl)-n-propylamino]thio]methylcarbamate;

2-isopropoxyphenyl [[diethoxyphosphinothioyl)-n-propylamino]methylcarbamate;

2-isopropoxyphenyl [[(diethoxyphosphinothioyl)-phenylamino]thio]methylcarbamate;

3-isopropylphenyl [[(diethoxyphosphinothioyl) isopropylamino]thio]methylcarbamate.

11. A process according to claim 4 wherein $R_1$ is lower alkyl.

12. A process according to claim 11 wherein both $Y_1$ and $Y_1'$ are lower-alkoxy.

13. A process according to claim 12 wherein the compound 1 prepared is selected from the group consisting of:

methyl N-[[[[(dimethoxyphosphinothioyl)methylamino]-thio]methylamino]carbonyl]oxy]ethanimidothioate;

methyl N-[[[[(dimethoxyphosphinothioyl)isopropylamino]thio]methylamino]carbonyl]oxy]ethanimidothioate;

methyl N-[[[[(dimethoxyphosphinothioyl)-n-butylamino]thio]methylamino]carbonyl]oxy]ethanimidothioate;

methyl N-[[[[(diethoxyphosphinothioyl)methylamino]-thio]methylamino]carbonyl]oxy]ethanimidothioate;

methyl N-[[[[(diethoxyphosphinothioyl)isopropylamino]thio]methylamino]carbonyl]oxy]ethanimidothioate;

methyl N-[[[[(diethoxyphosphinothioyl)-n-propylamino]thio]methylamino]carbonyl]oxy]ethanimidothioate;

methyl N-[[[[(diethoxyphosphinothioyl)anilino]thio]methylamino]carbonyl]oxy]ethanimidothioate.

14. A process according to claim 7 wherein R is an alkanimido group of the kind:

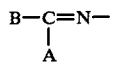

wherein A consists of hydrogen and lower-alkyl, and B consists of lower-alkylthio and lower alkylthio loweralkyl.

15. A process according to claim 14 wherein A is methyl, B is methylthio, $R_1$ is methyl, and $Y_1$ and $Y_1'$ are ethoxy so that Formula I is methyl N-[[[[(diethoxyphosphinyl)methylamino]thio]methylamino]carbonyl]oxy]ethanimidothioate.

16. A process according to claim 8 wherein R is an alkanimido group of the:

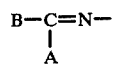

wherein A consists of lower-alkyl, B is lower-alkylthio, $Y_1$ is lower-alkylthio, $Y_1'$ is lower-alkoxy, and $R_1$ is lower alkyl.

17. A process according to claim 16 wherein $R_1$ is methyl, $Y_1$ is methylthio, $Y_1'$ is methoxy, A is methyl, and B is methylthio so that the specific embodiment is methyl N-[[[[[[methoxy(methylthio)phosphinyl]methylamino]-thio]methylamino]carbonyl]oxy]ethanimidotnioate.

18. A process according to claim 11 wherein R₁ is selected from the group consisting of lower alkyl and phenloweralkyl, Y₁ and Y₁' are different and are selected from the group consisting of lower-alkyl, loweralkoxy, phenyl, substituted phenyl, phenoxy and substituted phenoxy, thiophenoxy and substituted thiophenoxy.

19. A process according to claim 18 wherein the compound I prepared is selected from the group consisting of:
methyl N-[[[[[methoxy(phenyl)phosphinothioyl]isopropylamino]thio]methylamino]carbonyl]oxy]ethanimidothioate;
methyl N-[[[[[methoxy-(phenyl)phosphinothioyl]methylamino]thio]methylamino]carbonyl]oxy]ethanimidothioate;
methyl N-[[[[[methoxy(methyl)phosphinothioyl]methylamino]thio]methylamino]carbonyl]oxy]ethanimidothioate;
methyl N-[[[[[isopropoxy(phenyl)phosphinothioyl]isopropylamino]thio]methylamino]carbonyl]oxy]ethanimidothioate;
methyl N-[[[[methyl(phenoxy)phosphinothioyl]methylamino]carbonyl]oxy]ethanimidothioate;
methyl-N[[[[[isopropoxy(methyl)phosphinothioyl]isopropylamino]thio]methylamino]carbonyl]oxy]ethanimidothioate;
methyl N-[[[[[methoxy(methyl)phosphinothioyl]isopropylamino]thio]methylamino]carbonyl]oxy]ethanimidothioate;
methyl N-[[[[[methyl(phenoxy)phosphinothioyl]isopropylamino]thio]methylamino]carbonyl]oxy]ethanimidothioate;
methyl N-[[[[[4-chlorophenoxy(ethyl phosphinothioyl]isopropylamino]thio]methylamino]carbonyl]oxy]ethanimidothioate;
methyl [[[[[(1,1'-biphenyl-4-yloxy)ethylphosphinothioyl]isopropylamino]carbonyl]oxy]ethanimidothioate;
methyl N-[[[[[phenyl(phenoxy)phosphinothioyl]ethylamino]thio]methylamino]carbonyl]oxy]ethanimidothioate;
methyl N-[[[[[ethyl(phenoxy)phosphinothioyl]benzylamino]thio]methylamino]carbonyl]oxy]ethanimidothioate;
methyl N-[[[[[ethyl(phenoxy)phosphinothioyl]n-butylamino]thio]methylamino]carbonyl]oxy]ethanimidothioate.

20. A process according to claim 7 wherein R is:

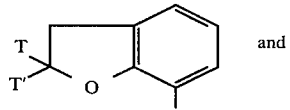 and wherein T and T' are methyl.

21. A process according to claim 20 wherein the compound I prepared is selected from the group consisting of
2,3-dihydro-2,2-dimethyl-7-benzofuranyl [(N-diethoxyphosphinyl)(N-methyl)-aminosulfenyl][methyl]carbamate;
2,3-dihydro-2,2-dimethyl-7-benzofuranyl [(N-di-n-propoxyphosphinyl)(N-methyl)aminosulfenyl][methyl]carbamate;
2,3-dihydro-2,2-dimethyl-7-benzofuranyl [N-di-n-propoxyphosphinyl)(N-n-propyl)aminosulfenyl][methyl]carbamate;
2,3-dihydro-2,2-dimethyl-7-benzofuranyl [(N-diethoxyphosphinyl) (N-n-propyl)aminosulfenyl][methyl]carbamate;
2,3-dihydro-2,2-dimethyl-7-benzofuranyl[(N-dimethoxyphosphinyl)(N-ethyl)aminosulfenyl][methyl]carbamate;
2,3-dihydro-2,2-dimethyl-7-benzofuranyl [(N-diisopropoxyphosphinyl)(N-methyl)aminosulfenyl][methyl]carbamate;
2,3-dihydro-2,2-dimethyl-7-benzofuranyl [(N-diethoxyphosphinyl) (N-ethyl)aminosulfenyl][methyl]carbamate.

22. A process according to claim 5 wherein R is:

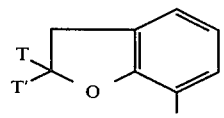 c.

wherein T and T' are methyl.

23. A process according to claim 22 wherein the compound I prepared is selected from the group consisting of
2,3-dihydro-2,2-dimethyl-7-benzofuranyl [(N-diphenoxyphosphinyl) (N-methyl)aminosulfenyl][methyl]carbamate;
2,3-dihydro-2,2-dimethyl-7-benzofuranyl [(N-diethoxyphosphinyl) (N-2-phenylethyl)aminosulfenyl][methylcarbamate].

24. A process according to claim 6 wherein the compound I prepared is selected from the group consisting of:
methyl N-[[[[[(diethoxyphosphinothioyl)-phenylamino]thio]methylamino]carbonyl]oxy]ethanimidothioate;
methyl N-[[[[[methyl(isopropoxy)phosphinothioyl]-phenylamino]thio]methylamino]carbonyl]oxy]ethanimidothioate;
methyl N-[[[[[ethyl(phenoxy)phosphinothioyl]benzylamino]thio]methylamino]carbonyl]oxy]ethanimidothioate;
methyl N-[[[[[ethyl(phenoxy)phosphinothioyl]4-chlorophenylamino]thio]methylamino]carbonyl]oxy]ethanimidothioate;
methyl N-[[[[[ethoxy(phenyl)phosphinothioyl]benzylamino]thio]methylamino]carbonyl]oxy]ethanimidothioate;
methyl N-[[[[[2-chlorophenoxy(ethyl)phosphinothioyl]anilino]thio]methylamino]carbonyl]oxy]ethanimidothioate;
methyl N-[[[[[4-chlorophenoxy(ethyl)phosphinothioyl]anilino]thio]methylamino]carbonyl]oxy]ethanimidothioate;
methyl N-[[[[[ethyl(phenoxy)phosphinothioyl]cyclohexylamino]thio]methylamino]carbonyl]oxy]ethanimidothioate.

25. A process according to claim 1 for preparing compounds having the formula:

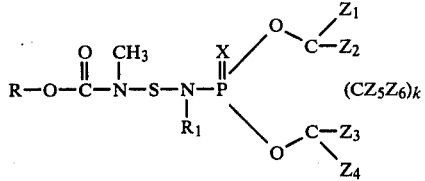

wherein R, R₁, k, X and Z₁ thru Z₆ are the same as in claim 1.

26. A process according to claim 25 wherein X is sulfur.

27. A process according to claim 25 wherein X is oxygen.

28. A process according to claim 26 wherein R is an alkanimido group of the kind

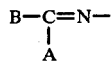

wherein A consists of lower alkyl and B consists of lower alkylthio.

29. A process according to claim 27 wherein R is:

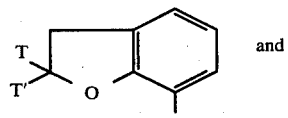

wherein T and T' are methyl.

30. A process according to claim 29 wherein Z₁ through Z₆ are hydrogen.

31. A process according to claim 28 wherein Z₅ and Z₆ are lower alkyl.

32. A process according to claim 28 wherein Z₁ through Z₆ are hydrogen.

33. A process according to claim 28 wherein Z₂, Z₅ and Z₆ are lower alkyl.

34. A process according to claim 31 wherein R₁ is lower alkyl.

35. A process according to claim 32 wherein R₁ is lower alkyl.

36. A process according to claim 33 wherein R₁ is lower alkyl.

37. A process according to claim 31 wherein R₁ is cycloalkyl.

38. A process according to claim 34 wherein the formula I' prepared is selected from the group consisting of:
methyl N-[[[[[isopropyl(5,5-dimethyl-2-thioxo-1,3,2-dioxaphosphorinan-2-yl)amino]thio]methylamino]-carbonyl]oxy]ethanimidothioate;
methyl N-[[[[[tert-butyl(5,5-dimethyl-2-thioxo-1,3,2-dioxphosphorinan-2-yl)amino]thio]methylamino]-carbonyl]oxy]ethanimidothioate;
methyl N-[[[[isopropyl(5,5-diethyl-2-thioxo-1,3,2-phosphorinan-2-yl)amino]thio]amino]carbonyl]oxy]ethanimidothioate;
methyl N-[[[[[ethyl(5,5-dimethyl-2-thioxo-1,3,2-dioxaphosphorinan-2-yl)amino]thio]methylamino]carbonyl]oxy]ethanimidothioate.

39. A process according to claim 35 wherein the formula I' prepared is selected from the group consisting of:
methyl N-[[[[[isopropyl(2-thioxo-1,3,2-phospholan-2-yl)amino]thio]methylamino]carbonyl]oxy]ethanimidothioate;
methyl-N-[[[[[isopropyl(2-thioxo-1,3,2-dioxaphosphorinan-2-yl)amino]thio]methylamino]carbonyl]oxy]ethanimdothioate.

40. A process according to claim 36 wherein the formula I' prepared is selected from the group consisting of:
methyl N-[[[[[isopropyl(4,4,6-trimethyl-2-thioxo-1,3,2-dioxaphosphorinan-2-yl)amino]thio]methylamino]carbonyl]oxy]ethanimidothioate.

41. A process according to claim 37 wherein the formula I' prepared is selected from the group consisting of:
methyl N-[[[[[cyclohexyl(5,5-diethyl-2-thioxo-1,3,2-dioxaphosphorinan-2-yl)amino]thio]methylamino]carbonyl]oxy]ethanimidothioate,
methyl N-[[[[[cyclohexyl(5,5-dimethyl-2-thioxo-1,3,2-dioxaphosphorinan-2-yl)amino]thio]methylamino]carbonyl]oxy]ethanimidothioate.

42. A process according to claim 30 wherein the formula I' prepared is 2,3-dihydro-2,2-dimethyl-7-benzofuranyl[[isopropyl(2-thioxo-1,3,2-dioxaphosphorinan-2-yl)amino]thio]methylcarbamate.

43. A process according to claim 35 wherein the formula I' prepared is
methyl N-[[[[[methyl(2-thioxo-1,3,2-dioxaphosphorinan-2-yl)amino]thio]methylamino]carbonyl]oxy]ethanimidothioate.

44. A process according to claim 1 for preparing compounds having the formula:

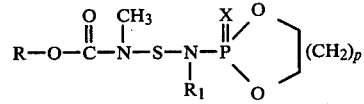

wherein R, R₁, X and P are the same as in claims 1.

45. A process according to claim 44 wherein X is sulfur.

46. A process according to claim 44 wherein X is oxygen.

47. A process according to claim 46 wherein the formula I'' prepared is 2-(1-methylethoxy)phenyl [[cyclopentyl(3a,4,5,6,7,7a-hexahydro-2-oxo-1,3,2-benzodioxaphosphol-2-yl)amino]thio]methylcarbamate.

48. A process according to claim 2 for preparing compounds having the formula:

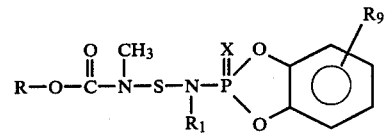

wherein R, R₁, X and R₉ are the same as in claim 2.

49. A process according to claim 48 wherein X is sulfur.

50. A process according to claim 48 wherein X is oxygen.

51. A process according to claim 49 wherein the formula I''' prepared is methyl N-[[[methyl[[(2-methylpropyl)(2-thioxo-1,3,2-benzodioxaphosphol-2-yl)amino]thio]amino]carbonyl]oxy]ethanimidothioate.

* * * * *

UNITED STATES PATENT OFFICE
CERTIFICATE OF CORRECTION

Patent No. 4,424,368            Dated January 3, 1984

Inventor(s) Stephen J. Nelson

It is certified that error appears in the above-identified patent and that said Letters Patent are hereby corrected as shown below:

Column 17, line 29 "according to claim 1" should read -- according to claim 53 (now claim 2) --.
Column 18, line 9 "propylamino]methylcarbamate" should read -- propylamino]-thio]methylcarbamate --.
Column 20, line 67 "according to claim 1" should read -- according to claim 53 (now claim 2) --.
Column 21, line 27 "according to claim 1" should read -- according to claim 27 (now claim 26) --.
Column 22, line 33 "according to claim 1" should read -- according to claim 53 (now claim 2) --.
Column 22, line 41 "as in claims 1" should read -- as in claim 53 (now claim 2) --.

Signed and Sealed this

Twentieth Day of September, 1988

Attest:

DONALD J. QUIGG

Attesting Officer      Commissioner of Patents and Trademarks